(12) United States Patent
Lee

(10) Patent No.: US 9,310,282 B2
(45) Date of Patent: Apr. 12, 2016

(54) IMPACT TESTING DEVICE

(71) Applicant: Kun-Ta Lee, New Taipei (TW)

(72) Inventor: Kun-Ta Lee, New Taipei (TW)

( * ) Notice: Subject to any disclaimer, the term of this patent is extended or adjusted under 35 U.S.C. 154(b) by 197 days.

(21) Appl. No.: 14/146,340

(22) Filed: Jan. 2, 2014

(65) Prior Publication Data
US 2015/0052971 A1    Feb. 26, 2015

(30) Foreign Application Priority Data
Aug. 26, 2013 (TW) .............................. 102130436 A

(51) Int. Cl.
*G01N 3/02* (2006.01)
*G01N 3/30* (2006.01)

(52) U.S. Cl.
CPC .. *G01N 3/02* (2013.01); *G01N 3/30* (2013.01); *G01N 2203/0033* (2013.01); *G01N 2203/0039* (2013.01)

(58) Field of Classification Search
CPC .............. G01N 3/30; G01N 2203/004; G01N 2203/003; G01N 2203/0039
See application file for complete search history.

(56) References Cited

U.S. PATENT DOCUMENTS

| | | | | |
|---|---|---|---|---|
| 3,836,098 A * | 9/1974 | Miyashita | ............. | B64C 27/001 188/380 |
| 5,284,058 A * | 2/1994 | Jones | ....................... | G01N 3/32 73/579 |
| 5,365,788 A * | 11/1994 | Hobbs | ..................... | G01M 7/06 73/665 |
| 5,434,549 A * | 7/1995 | Hirabayashi | ........... | H02K 33/00 335/229 |
| 5,517,857 A * | 5/1996 | Hobbs | ..................... | G01M 7/06 73/571 |
| 5,565,626 A * | 10/1996 | Davie | ....................... | G01N 3/30 73/579 |
| 5,589,637 A * | 12/1996 | Hobbs | ..................... | G01M 7/06 403/260 |
| 5,594,177 A * | 1/1997 | Hanse | .................... | G01M 7/027 73/663 |
| 5,804,732 A * | 9/1998 | Wetzel | ..................... | G01M 7/06 73/663 |
| 5,969,256 A * | 10/1999 | Hobbs | ..................... | G01M 7/06 73/662 |
| 6,105,433 A * | 8/2000 | Hess | ........................ | B06B 1/183 73/663 |
| 6,112,596 A * | 9/2000 | Hess | ........................ | B06B 1/183 73/663 |

(Continued)

FOREIGN PATENT DOCUMENTS

| CN | 202770615 U | 3/2013 |
|---|---|---|
| JP | 6293740 U | 6/1987 |

(Continued)

OTHER PUBLICATIONS

Japanese Office Action corresponding to Application No. 2013-203193; Mailing Date: Nov. 11, 2014, with English translation.

(Continued)

*Primary Examiner* — Lisa Caputo
*Assistant Examiner* — Tran M Tran
(74) *Attorney, Agent, or Firm* — Cantor Colburn LLP

(57) ABSTRACT

An impacting testing device is provided. The impacting testing device comprises a first platform, a second platform, a plurality of first suspension devices, at least one impact assembly and a plurality of second suspension devices. The at least one impact assembly is disposed on the second platform and faces the first platform for providing at least one impact force to the first platform, and thus, the impact testing is executed on an object disposed on the first platform.

18 Claims, 11 Drawing Sheets

(56) References Cited

U.S. PATENT DOCUMENTS

| | | | | |
|---|---|---|---|---|
| 6,220,100 B1* | 4/2001 | Felkins | ............... | G01M 7/022 73/663 |
| 6,247,366 B1* | 6/2001 | Porter | ............... | G01M 7/02 73/432.1 |
| 6,446,508 B1 | 9/2002 | Peterson et al. | | |
| 6,860,152 B2* | 3/2005 | Lund | ............... | G01M 7/06 73/663 |
| 7,487,680 B2* | 2/2009 | Hammond | ............... | G01M 7/02 73/663 |
| 7,913,573 B2* | 3/2011 | Schulz et al. | ............... | 73/856 |
| 8,061,677 B2* | 11/2011 | Johnson | ............... | F16F 7/1011 248/550 |
| 8,240,214 B2* | 8/2012 | Lee | ............... | G01M 7/08 73/12.09 |
| 8,306,796 B2* | 11/2012 | Lee | ............... | G01M 7/022 703/6 |
| 8,429,975 B2* | 4/2013 | Lee | ............... | G01M 7/022 73/663 |
| 8,453,512 B2* | 6/2013 | Sasso | ............... | G01C 19/72 73/663 |
| 8,902,578 B2* | 12/2014 | Lee | ............... | G11B 33/08 361/679.34 |
| 2011/0006619 A1* | 1/2011 | Lee | ............... | H02K 33/16 310/30 |
| 2013/0000381 A1* | 1/2013 | Lee | ............... | G01M 7/022 73/12.09 |
| 2013/0283885 A1* | 10/2013 | Lee | ............... | G01N 3/307 73/12.04 |

FOREIGN PATENT DOCUMENTS

| | | |
|---|---|---|
| JP | 201344744 A | 3/2013 |
| TW | 490016 U | 6/2002 |
| TW | 392957 U1 | 11/2010 |
| WO | 2004037400 A2 | 5/2004 |

OTHER PUBLICATIONS

Taiwanese Office Action corresponding to Application No. 102130436; Mailing Date: Nov. 5, 2014, with English translation.

* cited by examiner

IMPACT TESTING DEVICE

CROSS-REFERENCES TO RELATED APPLICATIONS

The present invention claims priority under 35 U.S.C. §119 Taiwan Patent Application No. 102130436 filed on Aug. 26, 2013, the entire content of which is incorporated herein by reference.

BACKGROUND OF THE INVENTION

1. Field of the Invention

The present invention provides a testing device; and more particularly, to an impact testing device.

2. Descriptions of the Related Art

Impacting testing devices are used to measure the reliability of products in the following principle: a regular or irregular impacting force is generated by an impact testing device to impact an object under testing (i.e., a product). Then, through accumulative impact fatigue over a long period of time, potential defects in the object undergoing testing can be measured to evaluate the internal components and structures or the protection level of outer packages as a basis of improving reliability in use and product quality.

In the conventional impact testing device, the object undergoing testing is placed on a platform of the impact testing device and, then, by means of at least one impact assembly disposed under the platform, an impact test is executed on the platform and the object undergoing testing to measure the potential defects after impact. Although this approach of using at least one impact assembly to impact the object undergoing testing from bottom to top can provide related impact testing data, the impact force generated by the at least one impact assembly is imposed on both the platform and the object undergoing testing simultaneously during the impact process. Therefore, a part of the impact force (or even most part of the impact force) is absorbed by the platform and consumed by actions unrelated to the impact test.

On the other hand, according to Newton's Third Law of Motion, when two objects interact with each other, the forces applied to each other have the same magnitude and opposite directions. For this reason, Newton's Third Law of Motion is also called "Law of Acting Force and Reacting Force". According to this law, when an impact test is executed by at least one impact assembly to generate an impact force to the platform, a reacting force will also be generated to the at least one impact assembly. Consequently, because both the platform and the at least one impact assembly belong to the impact testing device and their spatial positions are associated with each other, a reacting force will be generated to the at least one impact assembly according to Newton's Third Law of Motion when the impact force is applied by the at least one impact assembly to the object undergoing testing. The reacting force will indirectly cause impact to the platform and the object undergoing testing to affect the final testing results. This effect is particularly significant when the at least one impact assembly is a single impact assembly and comprises a plurality of impact hammers.

The following case in which a single impact assembly comprises two impact hammers (i.e., a first impact hammer and a second impact hammer) disposed opposite each other and the two impact hammers impact the platform obliquely at an angle of 45° respectively will be used as an example. If the two impact hammers impact the platform in sequence, a reacting force generated according to Newton's Third Law of Motion will be applied to the second impact hammer after impact from the first impact hammer has been completed but before the impact from the second impact hammer begins. This reacting force will affect the impact force imposed by the second impact hammer on the platform and cause measurement errors.

Errors may also be caused if there is insufficient time between the impact of the first impact hammer and the second impact for the platform to restore its initial stationary position. In this case, the minor displacement of the platform may also affect the testing results.

As can be known from the above descriptions, although the conventional impacttesting devices can measure potential defects after the object undergoing testing is impacted, numerous variables or instable factors still exist in the testing process. As a result, it is difficult to achieve precise control and accurate results.

Additionally, the stress produced at the instant of impact by the impact hammers excites a natural response in the object undergoing testing. When the object undergoing testing is a device or a system comprised of a plurality of elements, the stress produced at the instant of impact by the impact hammers excites a natural response of each of the elements. As has been found through research, interferences between the natural responses between individual elements are actually the most prominent factor that causes damage to the elements or the system.

In other words, because conventional impact testing devices cannot accurately control the impacting on the object undergoing testing, it is difficult to establish a shock response spectrum (SRS) by measuring interferences between the natural responses of the individual elements. It is also difficult to accurately determine the reliability and service life of the object undergoing testing.

Accordingly, it is important to provide an impact testing platform which, during impact testing, can effectively eliminate influences of the aforesaid acting force and reacting force and minimize the displacement of the platform to make the impact testing results accurate.

SUMMARY OF THE INVENTION

An objective of the present invention is to provide an impact testing device, in which at least one impact assembly of the impact testing device comprises a plurality of first impact hammers and/or a second impact hammer. The plurality of first impact hammer is disposed on a second platform obliquely at a certain angle, while the second impact hammer is perpendicular to the second platform. In this way, the impact forces in multiple axial directions can be provided to satisfy the needs of different impact tests.

Another objective of the present invention is to provide an impact testing device, in which a plurality of first suspension devices of the impact testing device is adapted to bear a first platform on which an object undergoing testing is placed. In this way, the first platform will only displace very slightly during the impact testing process. Thus, impact testing data can be obtained accurately and the SRS of the object under testing can be established according to the impact testing data.

Yet a further objective of the present invention is to provide an impact testing device, in which a plurality of second suspension devices of the impacting testing device can effectively absorb the generated reacting force when impact is imposed by the at least one impact assembly. In this way, interference to the at least one impact assembly can be reduced and transfer of the impact to the outside can be prevented.

To achieve the aforesaid objectives, the present invention discloses an impact testing device, which comprises a first platform, a second platform, a plurality of first suspension device, at least one impact assembly and a plurality of second suspension devices. The first platform is adapted to bear the object, while the second platform is disposed under and parallel to the first platform. The plurality of first suspension devices is disposed between the first platform and the second platform for bearing the first platform. The impact assembly is disposed on the second platform and faces the first platform for providing the impact force to the first platform. The plurality of second suspension devices is opposite the first suspension devices and disposed under the second platform. The second suspension devices are used for bearing the first platform, the second platform, the first suspension devices and the at least one impact assembly to absorb at least one reacting force generated by the at least one impact force when the test is executed.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
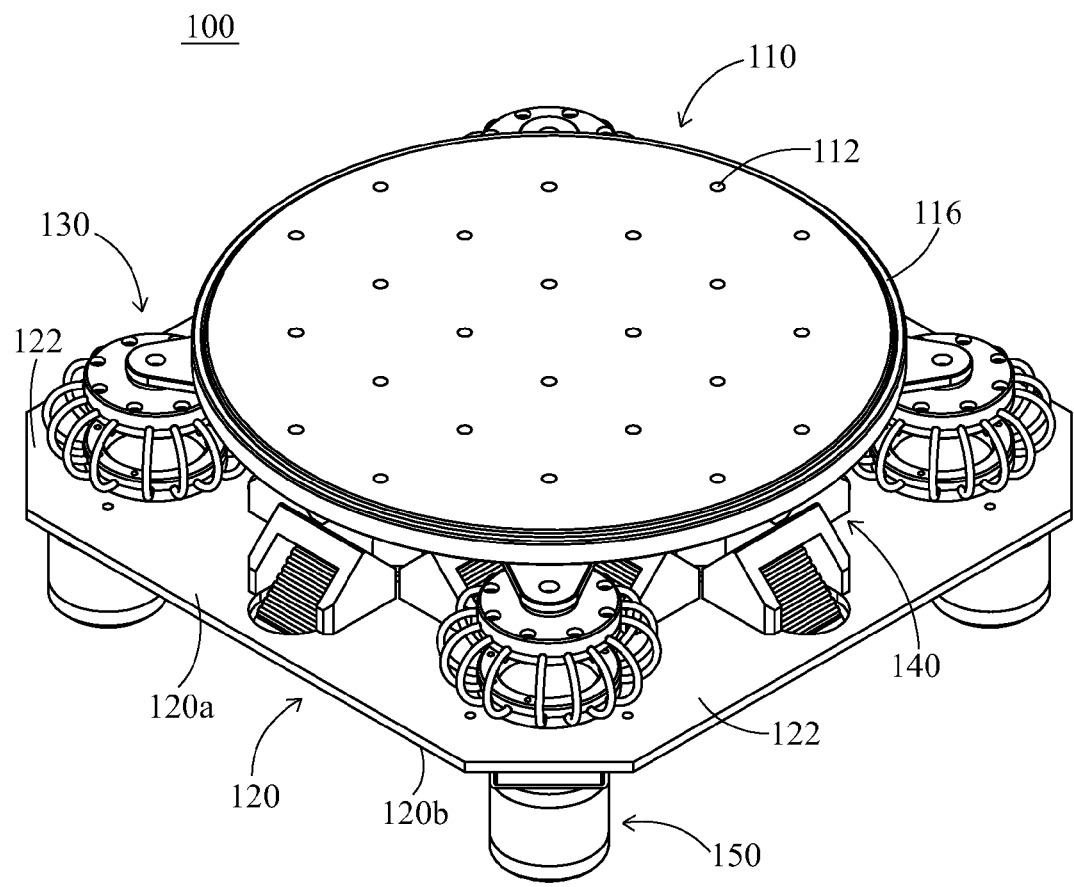
FIG. 1 is a schematic view of an impacting testing device according to the present invention.

As shown in FIG. 1, an impacting testing device 100 of the present invention is adapted to bear an object undergoing testing (not shown) to execute an impact test. The impact testing device 100 comprises a first platform 110, a second platform 120, a plurality of first suspension devices 130, at least one impact assemblies 140 and a plurality of second suspension devices 150.

Hereinbelow, positional relationships between the first platform 110, the second platform 120, the first suspension devices 130, the at least one impact assembly 140 and the second suspension devices 150 will be described.

Figure 2:
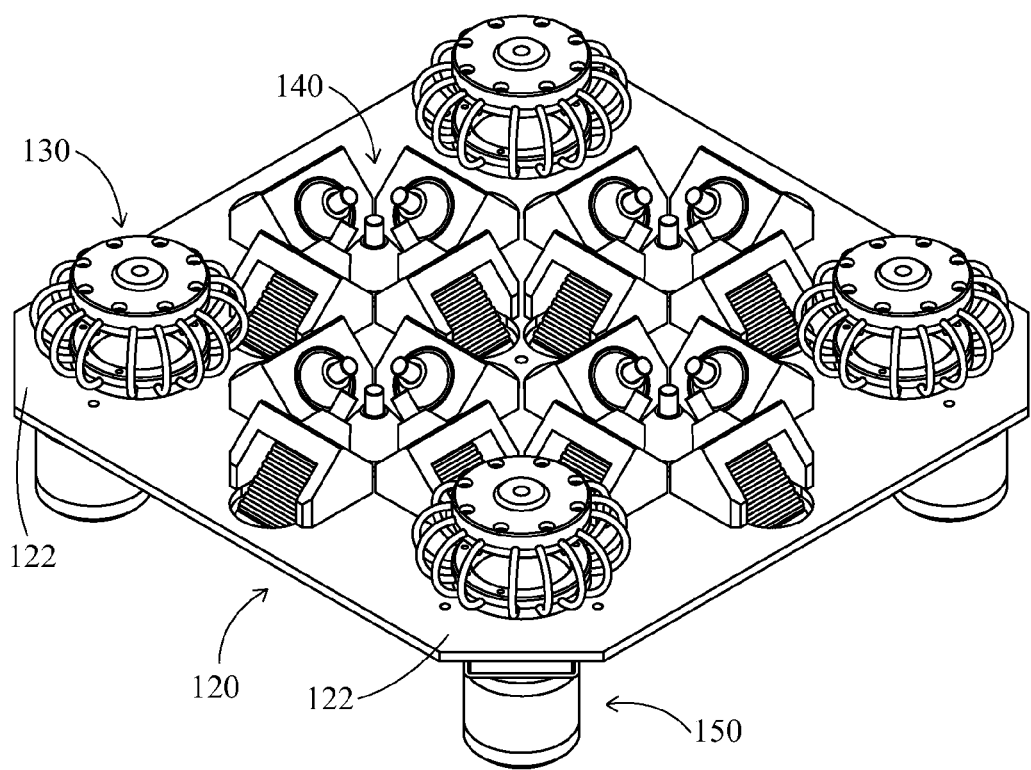
FIG. 2 is a schematic view of the impacting testing device according to the present invention when the first platform is not equipped.

As shown in FIG. 1 and FIG. 2, the first platform 110 is adapted to bear the object undergoing testing and, by means of a plurality of fixing holes 112, fix the object thereon securely. The second platform 120 is parallel to the first platform 110 and disposed under the first platform 110. The first suspension devices 130 are disposed between the first platform 110 and the second platform 120 for bearing the first platform 110 from below. The at least one impact assembly 140 is disposed on the second platform 120 and faces the first platform 110 so that when a signal is received, at least one impact force is generated to impact the first platform 110. The second suspension devices 150 are opposite the first suspension devices 130 and disposed under the second platform 120.

The first suspension devices 130 preferably include four first suspension devices 130 and are disposed at the periphery 122 of the second platform 120 to securely bear the first platform 110 from below.

With reference to FIG. 2, in the impacting testing device 100 of the present invention, the first suspension devices 130 and the second suspension devices 150 are disposed on two sides of the second platform 120 (i.e., an upper side 120a facing the first platform 110 and lower side 120b opposite the upper side 120a) respectively. Therefore, the second suspension device 150 disposed on the lower side 120b of the second platform 120 can be used to bear the first platform 110, the second platform 120, the first suspension devices 130 and the at least one impact assembly 140, and can effectively absorb at least one reacting force generated against the at least one acting force of the at least one impact assembly 140 during the impact test to prevent the transfer of the reacting force to the outside.

In the embodiment shown in FIG. 1 and FIG. 2, the at least one impact assembly includes a plurality of impact assemblies, which is four impact assemblies 140 herein. Additionally, each of the impact assemblies 140 comprises at least one first impact hammer 142 and a second impact hammer 144. Preferably, in an embodiment shown in FIG. 3, the at least one first impact hammer 142 includes four first impact hammers 142, which are opposite each other in groups of two and are disposed on the second platform 120 obliquely at a certain angle. The second impact hammer 144 is disposed between the four first impact hammers 142.

Figure 3:
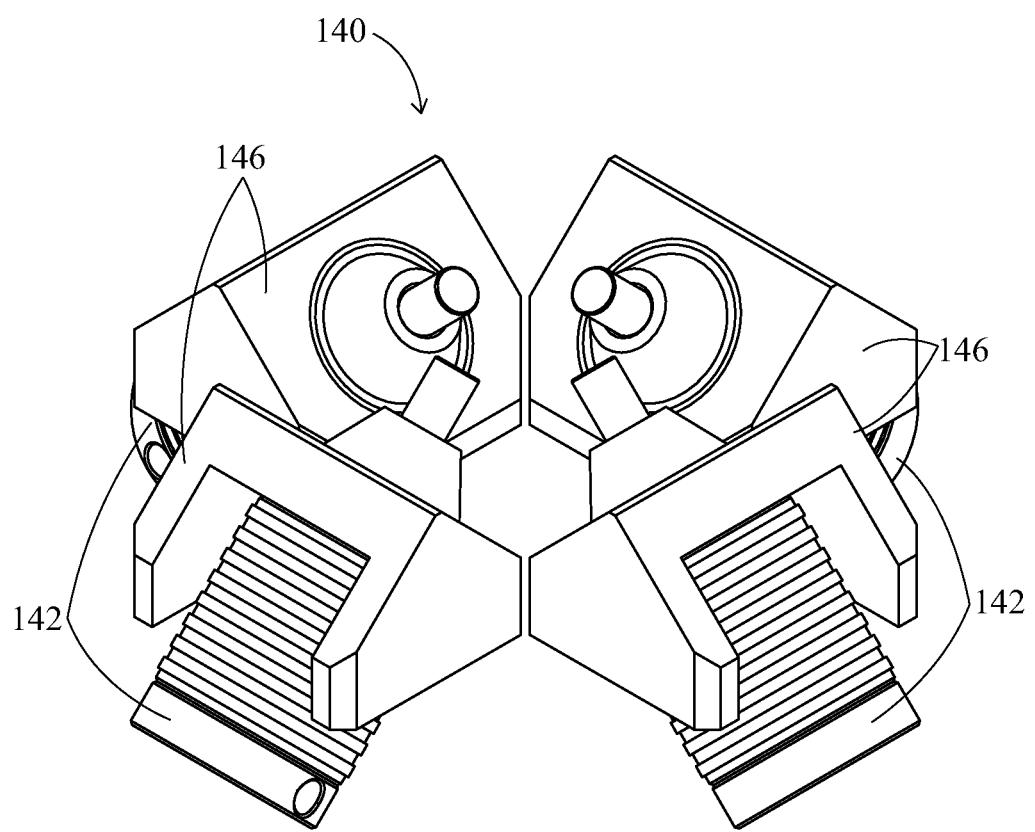
FIGS. 3 and 4 are schematic views of the first embodiment of at least one impact assembly of the impacting testing device according to the present invention.
Figure 4:
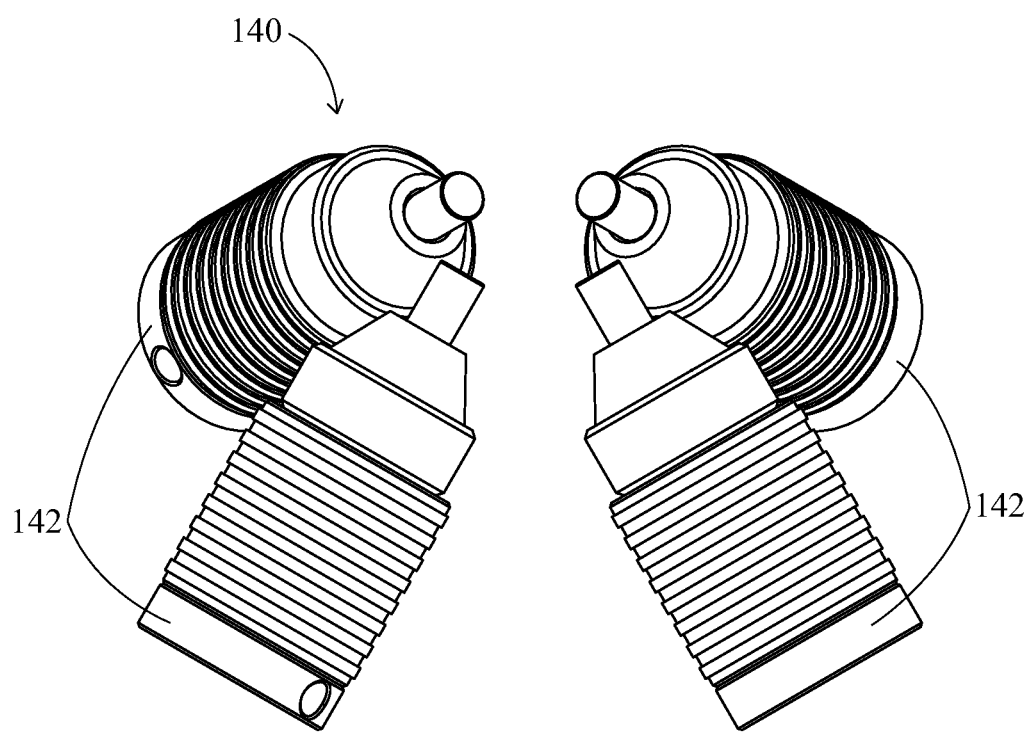

Specifically, in the first embodiment of the at least one impact assembly 140 as shown in FIG. 3 and FIG. 4, the four first impact hammers 142 are all disposed on the second platform 120 obliquely at a certain angle with respect to the second platform 120 and are opposite to each other in groups of two. Disposing the first impact hammers 142 obliquely at a certain angle may be accomplished by fixing each of the first impact hammers 142 to an angle adaptation mount 146. In this embodiment, the certain angle is 45°. It shall be appreciated that FIGS. 3 and 4 are both used to illustrate the first embodiment of the at least one impact assembly 140 and differ from each other only in that the depiction of the angle adaptation mount 146 is omitted in FIG. 4 to illustrate the spatial positional relationships between the first impact hammers 142 more clearly.

Therefore, when the four first impact hammers 142 are disposed on the second platform 120 obliquely at an angle of 45°, the four first impact hammers 142 will also be oblique at an angle of 45° with respect to the first platform 110 because the second platform 120 is parallel to the first platform 110. After receiving a signal, the four impact hammers 142 can, according to the contents of the signal, generate impact forces in sequence or simultaneously to directly impact the first platform 110 obliquely at an angle of 45°.

Of course, apart from being oblique at an angle of 45°, the four first impact hammers 142 may also be oblique at other angles with respect to the second platform 120 depending on different testing requirements, so the oblique angle is not limited thereto.

Figure 5:
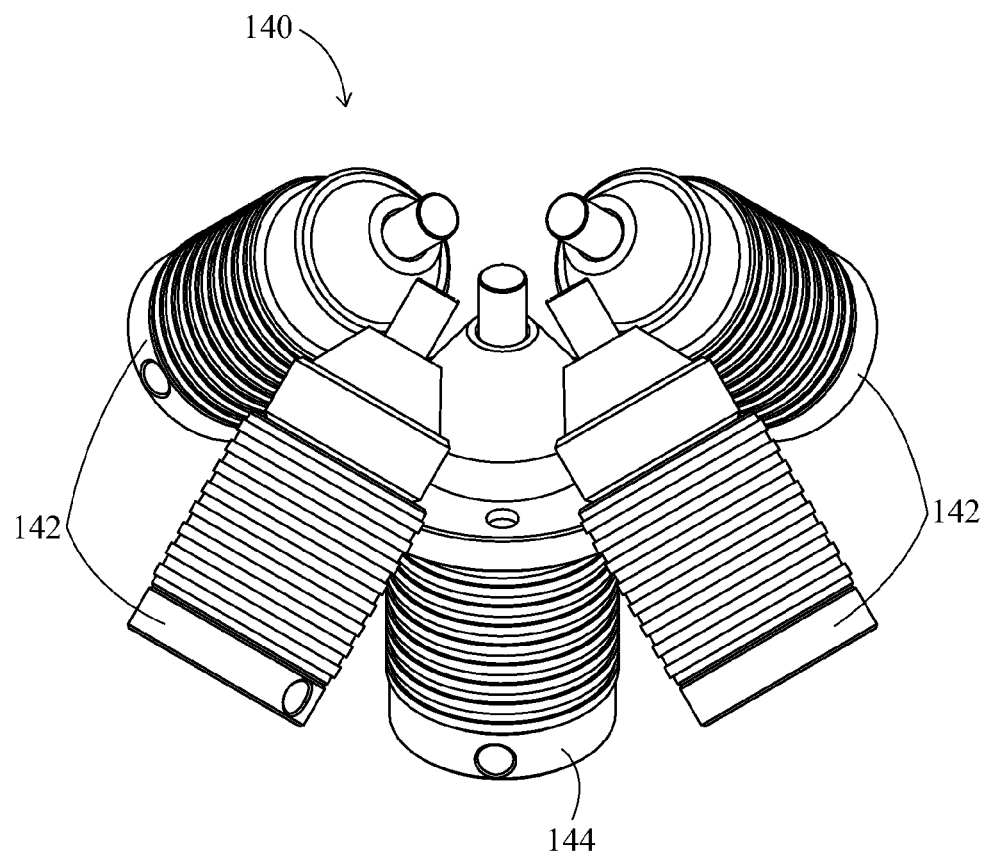
FIG. 5 is a schematic view of the second embodiment of at least one impact assembly of the impacting testing device according to the present invention.

In the second embodiment of the at least one impact assembly 140 as shown in FIG. 5, the impact assembly 140 may further comprise a second impact hammer 144, which is disposed perpendicularly on the second platform 120 and surrounded by the four first impact hammers 142.

When the second impact hammer 144 is installed, the application of a vertical impact force to the object undergoing testing disposed on the first platform 110 can be accomplished by simply providing a signal to operate the second impact hammer 144 so that an impact force is generated to vertically impact the first platform 110 directly. This eliminates the need of providing a signal to operate the four first impact hammers 142 simultaneously to obtain a vertical resultant force to impact the first platform 110 as in the first embodiment of the at least one impact assembly 140 shown in FIGS. 3 and 4. In other words, in cases where vertical impact tests are performed frequently, disposition of the second impact hammer 144 helps to save the power.

In addition to the first embodiment and the second embodiment of the at least one impact assembly 140, those of ordinary skill in the art may also alter the number(s) and orientations of the first impact hammers 142 and/or the second impact hammer 144 as desired to provide an impact force of any direction and any magnitude. Thereby, impact forces in multiple axial directions can be provided to satisfy needs of different impact tests.

On the other hand, in the first embodiment and the second embodiment of the at least one impact assembly 140 shown in FIGS. 3, 4 and 5, the first platform 110 is impacted directly by the first impact hammers 142 and/or the second impact hammer 144. In this process of impacting the first platform 110 by the first impact hammers 142 obliquely at a certain angle, the impact forces will be scattered and attenuated more or less because the directions of the impact forces generated by the first impact hammers 142 are not orthogonal to the first platform 110. This will seriously affect the impact testing results.

Figure 6:
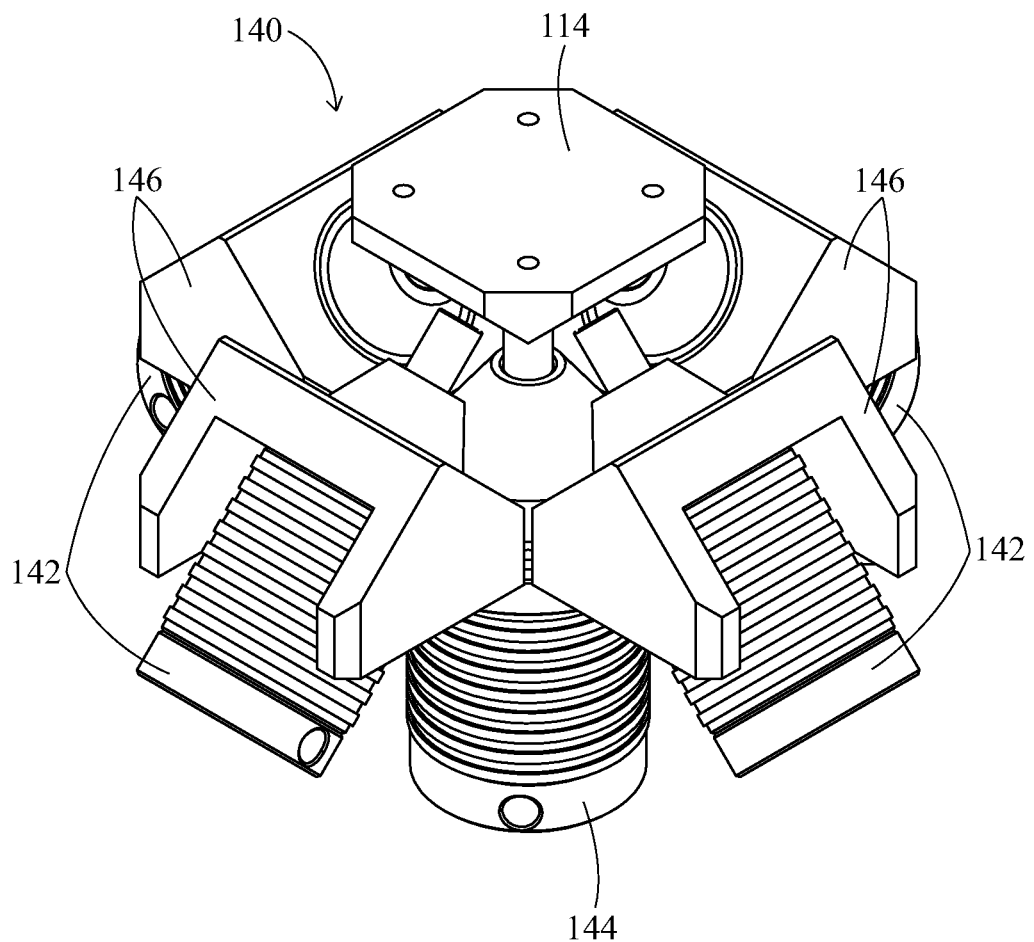
FIGS. 6 and 7 are schematic views illustrating how the at least one impact assembly and at least one impacted block are disposed in the impacting testing device according to the present invention.
Figure 7:
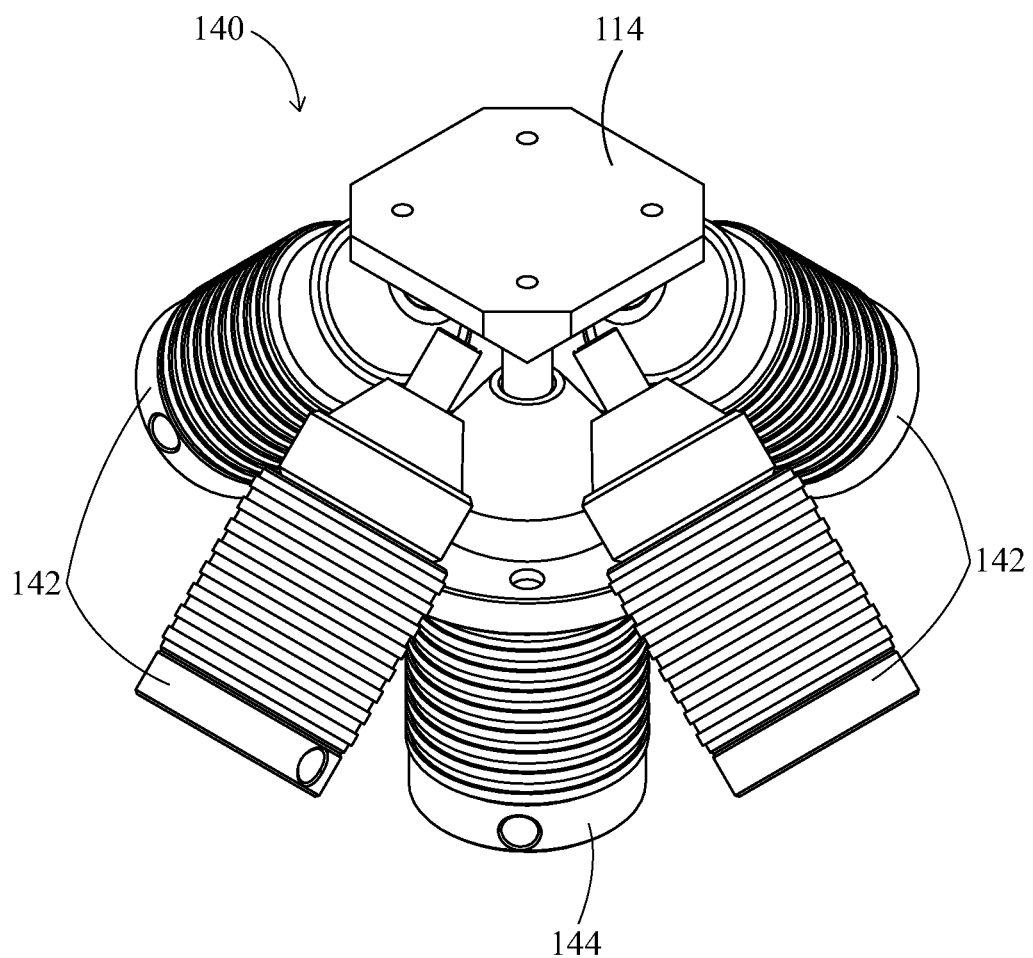

To prevent scattering and attenuation of the impact forces, the first platform 110 further comprises at least one impacted block 114 as shown in FIGS. 6 and 7. The at least one impacted block 114 is disposed under the first platform 110 and each has a surface 114a orthogonal to the respective first impact hammer 142 and/or the second impact hammer 144. Thus, when each of the first impact hammers 142 and/or the second impact hammer 144 is operated, the direction of the impact force generated is orthogonal to the impacted block 114 and transferred to the first platform 110 to impact the first platform 110 without attenuation.

Figure 8:
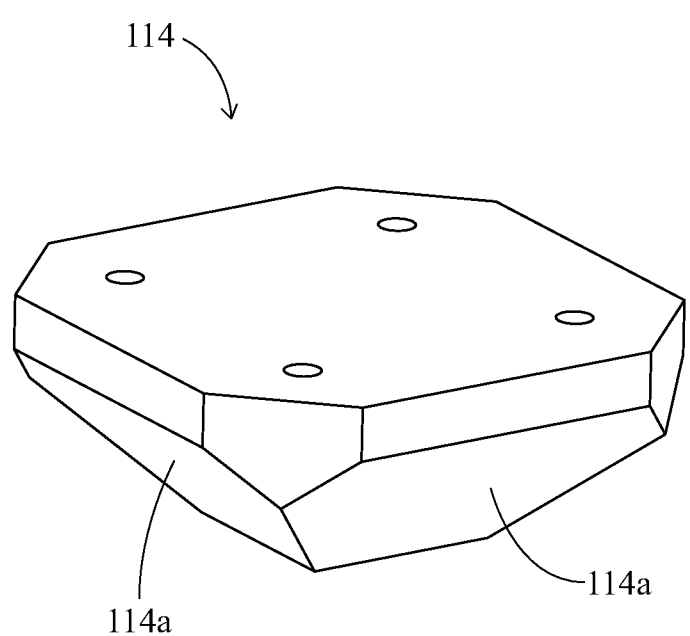
FIG. 8 is a schematic view of an impacted block of the impacting testing device according to the present invention.

Accordingly, in the embodiments of the present invention, the number of impacted blocks 114 corresponds to the number of the impact assemblies 140, and as shown in FIG. 8, each of the impacted blocks 114 is preferably in the form of a polyhedron with a plurality of impacted surfaces 114 (e.g., an angled block). Of course, each of the impacted blocks 114 may also be in the form of a hemisphere or a cube. The present invention has no limitation on the form as long as the impacted block 114 has surfaces orthogonal to each of the first impact hammers 142 and/or the second impact hammer 144.

In addition to the embodiment shown in FIGS. 1 and 2 where the at least one impact assembly includes four impact assemblies 140, an embodiment in which the at least one impact assembly includes only a single impact assembly 140 that comprises four first impact hammers 142 disposed obliquely at a certain angle and a second impact hammer 144 disposed perpendicularly may also be contemplated out of economical considerations.

It shall be appreciated that because the positional relationships between the single impact assembly 140 and the first platform 110 and the second platform 120 are similar to those of the embodiments where a plurality of impact assemblies 140 is included, these positional relationships will not be described again herein. Similarly, the number(s) and oblique angles of the first impact hammers 142 and the second impact hammer may also be adjusted depending on different testing requirements, so there is not limitation thereon herein.

To satisfy the needs of obtaining accurate impact testing data, conventional air hammers cannot be used as the first impact hammers 142 and the second impact hammer 144; instead, electromagnetic hammers operated by electronic signals need to be used to accurately control the strength and frequency of the impact.

Additionally, apart from fixing the object undergoing testing by means of the plurality of fixing holes 112, the fixing holes 112 may also be replaced by a plurality of vacuum suction holes to adsorb the object undergoing testing with the same fixing effect. The first platform 110 may further have a rotating mechanism 116 disposed under the first platform 110 to drive the first platform 110 to rotate horizontally relative to the second platform 120. This movement facilitates inspection of the testing staff during the impact test.

Figure 9:
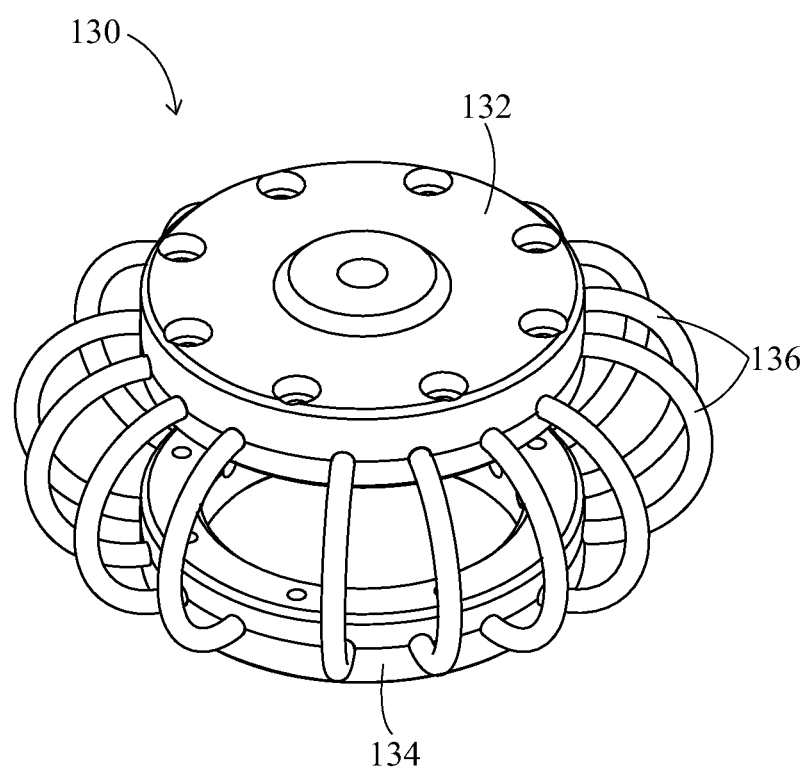
FIG. 9 is a schematic view of the first suspension device of the impacting testing device according to the present invention.

As shown in FIG. 9, each of the first suspension devices 130 has a top portion 132, a bottom portion 134 opposite the top portion 132 and a plurality of coils 136 supported between the top portion 132 and bottom portion 134. With reference to FIG. 1, the top portion 132 and the bottom portion 134 are adapted to be fixed to the first platform 110 and the second platform 120 respectively. The coils 136 are adapted to support the first platform 110 and the object undergoing testing disposed on the first platform 110.

As shown in FIG. 9, as the coils 136 of the first suspension devices 130 are made of steel tubes or steel ropes and has superior shock resistance, each of the first suspension devices 130 consisting of the top portion 132, the bottom portion 134 and plurality of coils 136 will form a special spherical structure so that when the first suspension device 130 is used to support the first platform 110 on which the object undergoing testing is disposed, the first platform 110 will displace only very slightly during the impact test. Thus, impact testing data can be obtained accurately and the SRS of the object under test can be established according to the impact testing data.

Figure 10:
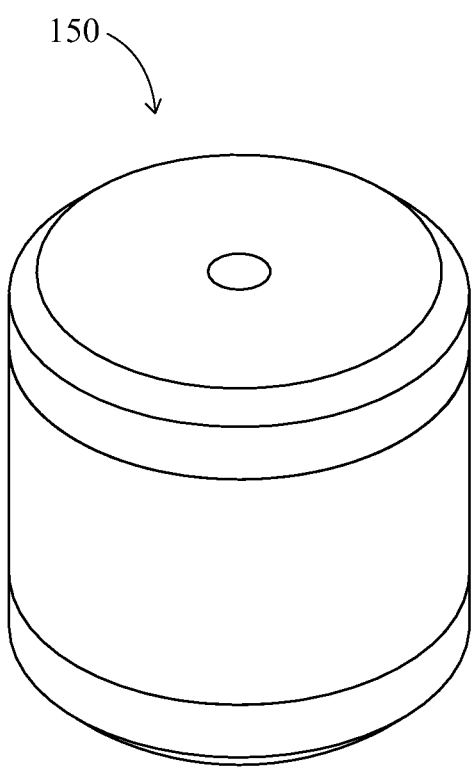
FIG. 10 is a schematic view of the second suspension device of the impacting testing device according to the present invention.

As shown in FIG. 10, the second suspension devices 150 are used to support the first platform 110, the second platform 120, the first suspension devices 130 and the at least one impact assembly 140 to effectively absorb the reacting force generated by the impacting action of the at least one impact assembly 140 during the impact test so that interferences to the at least one impact assembly 140 during operation can be reduced to obtain accurate impact testing data. For this reason, the second suspension devices 150 are preferably comprised of a silicone base, and are made of silicone, rubber, plastic, foam or other materials with a shock-absorbing effect to prevent transfer of the impact to the outside.

Figure 11:
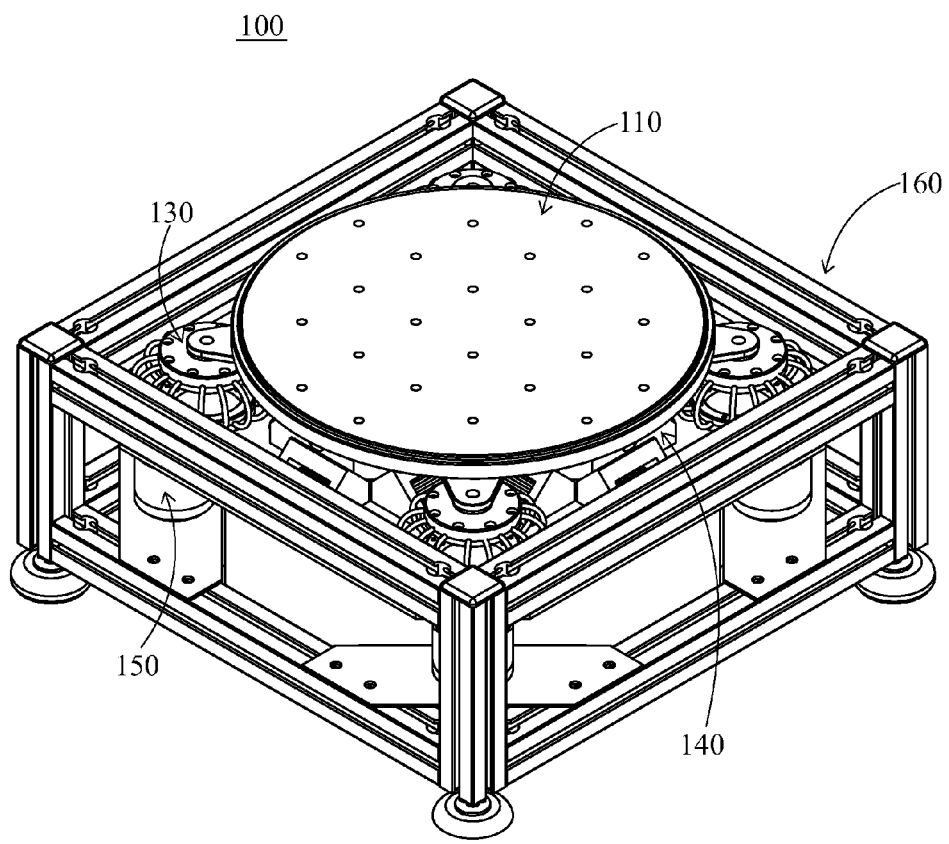
FIG. 11 is a schematic view illustrating a case when the impacting testing device according to the present invention is disposed in a frame.

As shown in FIG. 11, the impact testing device 100 of the present invention may further comprise a frame 160 for accommodating the first platform 110, the second platform 120, the first suspension devices 130, the at least one impact assembly 140 and the second suspension devices 150. This can enhance the effect of isolation from the outside and improve the portability.

Although the first platform 110 is illustrated as a circular platform and the second platform 120 is illustrated as a generally rectangular platform in the embodiment shown in FIGS. 1 and 2, this is not intended to limit the shapes of the first platform 110 and the second platform 120. Those of ordinary sill in the art may also modify the shapes of the first platform 110 and the second platform 120 readily, so the present invention has no limitation thereon.

According to the above descriptions, the at least one impact assembly 140 of the impacting testing device 100 of the present invention comprises at least one first impact hammer 142 and/or a second impact hammer 144. The at least one first impact hammer 142 may be oblique at a certain angle with respect to the second platform 120. The second impact hammer 144 is perpendicular to the second platform 120. Therefore, through the combination of the at least one first impact hammer 142 and the second impact hammer 144, impact forces in multiple axial directions can be provided to satisfy the needs of different impact tests.

On the other hand, by disposing the first suspension devices 130 to support the first platform 110 on which the object undergoing testing is disposed, the first platform 110 is displaced only very slightly during the impact test. Thereby, impact testing data can be obtained accurately and the SRS of the object under test can be established according to the impact testing data.

Furthermore, by disposing the second suspension devices 150, the reacting force generated by the impacting action of the at least one impact assembly 140 can be effectively absorbed during the impact test so that interferences to the at least one impact assembly 140 during operation can be reduced. Meanwhile, transfer of the impact to the outside can be prevented.

Thereby, by means of the plurality of ultra-small high-efficiency impact assemblies 140 of the impact testing device 100 of the present invention, acting forces can be generated without time differences and with accuracy to impact the object undergoing testing on the first platform 110. In this way, the SRS of the object undergoing testing can be measured to keep track of the primary factor that causes damage during the impact so that according to the SRS result, reliability of the object undergoing testing can be improved to prolong the service life thereof.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An impacting testing device for executing an impact test on an object when the impacting testing device bears the object, comprising:
   a first platform for bearing the object;
   a second platform disposed under and parallel to the first platform;
   a plurality of first suspension devices disposed between the first platform and the second platform for bearing the first platform;
   at least one impact assembly disposed on the second platform and facing the first platform for providing at least one impact force to the first platform;
   a plurality of second suspension devices opposite the first suspension devices and disposed under the second platform; and
   a frame for accommodating the first platform, the second platform, the first suspension devices, the at least one impact assembly and the second suspension devices;
   wherein the second suspension devices are used for bearing the first platform, the second platform, the first suspension devices and the at least one impact assembly in order to absorb at least one reacting force generated by the at least one impact force when the test is executed.

2. The impacting testing device according to claim 1, wherein the at least one impact assembly comprises an impact assembly and the impact assembly comprises at least one impact hammer.

3. The impacting testing device according to claim 2, wherein the at least one impact hammer comprises four first impact hammers, two of which are disposed opposite to each other and the other two of which are disposed also opposite to each other.

4. The impacting testing device according to claim 3, wherein the impact assembly further comprises a second impact hammer disposed between the four first impact hammers.

5. The impacting testing device according to claim 1, wherein the at least one impact assembly comprises a plurality of impact assemblies, the impact assemblies are four impact assemblies and each of the impact assemblies comprises at least one first impact hammer.

6. The impacting testing device according to claim 5, wherein the at least one first impact hammer comprises four first impact hammers, two of the four first impact hammers are disposed opposite to each other and the other two of which are disposed also opposite to each other.

7. The impacting testing device according to claim 6, wherein each of the impact assemblies further comprises a second impact hammer disposed between the four first impact hammers.

8. The impacting testing device according to claim 3 or 6, wherein the four first impact hammers are disposed on the second platform and are oblique relative to the second platform at a specific angle.

9. The impacting testing device according to claim 4 or 7, wherein the second impact hammer is disposed perpendicularly to the second platform.

10. The impacting testing device according to claim 1, wherein the first platform comprises a plurality of fixing holes and at least one impacted block which is disposed under the first platform to be impacted by the at least one impact assembly.

11. The impacting testing device according to claim 10, wherein the at least one impacted block is a hemisphere, a polyhedron or a cube.

12. The impacting testing device according to claim 1, wherein the first suspension devices are disposed on a periphery of the second platform.

13. The impacting testing device according to claim 1, wherein the first platform is a rectangular platform or a circular platform and comprises a rotating mechanism for driving the first platform to rotate relative to the second platform.

14. The impacting testing device according to claim 1, wherein the second platform is a rectangular platform or a circular platform.

15. The impacting testing device according to claim 1, wherein each of the first suspension devices has a top portion, a bottom portion opposite the top portion and a plurality of coils supported between the top portion and bottom portion, the top portion and the bottom portion are adapted to be fixed to the first platform and the second platform respectively and the coils are adapted to support the first platform.

16. The impacting testing device according to claim 15, wherein the coils of the first suspensions devices are made of steel tubes or steel ropes.

17. The impacting testing device according to claim 1, wherein the second suspension devices are silicone pedestals.

18. The impacting testing device according to claim 17, wherein the second suspension devices are made of silicone, rubber, plastic or foam.

* * * * *